US009907628B2

(12) United States Patent
Katto

(10) Patent No.: US 9,907,628 B2
(45) Date of Patent: Mar. 6, 2018

(54) IMPLANTS FOR AN ARTIFICIAL TOOTH

(71) Applicant: Tosa Enterprise Co., Ltd., Tokyo (JP)

(72) Inventor: Akinori Katto, Tokyo (JP)

(73) Assignee: TOSA ENTERPRISE CO., LTD., Tokyo (JP)

(*) Notice: Subject to any disclaimer, the term of this patent is extended or adjusted under 35 U.S.C. 154(b) by 288 days.

(21) Appl. No.: 14/501,849

(22) Filed: Sep. 30, 2014

(65) Prior Publication Data
US 2015/0111174 A1 Apr. 23, 2015

(30) Foreign Application Priority Data

Oct. 17, 2013 (JP) .................................. 2013-216592
Nov. 5, 2013 (JP) .................................. 2013-229041
May 27, 2014 (JP) .................................. 2014-109085

(51) Int. Cl.
A61C 8/00 (2006.01)
(52) U.S. Cl.
CPC ............. A61C 8/001 (2013.01); A61C 8/005 (2013.01); A61C 8/0028 (2013.01);
(Continued)
(58) Field of Classification Search
CPC ....... A61C 8/00; A61C 8/0028; A61C 8/0027; A61C 8/001; A61C 8/0043; A61C 8/0045; A61C 8/05; A61C 8/0048; A61C 8/005
See application file for complete search history.

(56) References Cited

U.S. PATENT DOCUMENTS

2005/0053894 A1* 3/2005 Wu ........................ A61C 5/08
433/18
2009/0258329 A1* 10/2009 Adams .................. A61C 8/001
433/174
2011/0033825 A1* 2/2011 Lee ..................... A61B 17/8625
433/173

FOREIGN PATENT DOCUMENTS

JP       6-178784       6/1994
JP       3678653        5/2005
(Continued)

OTHER PUBLICATIONS

Peikoff, et al, "The maxillary second molar: variations in the number of roots and canals", Int Endod J, Nov. 1996; 29(6): 365-9, abstract only.*

Primary Examiner — Leslie Lopez
(74) Attorney, Agent, or Firm — Wenderoth, Lind & Ponack, L.L.P.

(57) ABSTRACT

The present invention is to provide implants for an artificial tooth that does not require a period, for integration of implant bodies and a jawbone as in the background art, enables treatment even of a patient whose jawbone is small in bone amount or thickness, can reduce the treatment period and the number of times of treatment for many patients, and can lighten the mental and physical burden of a patient by minimizing the impact to the jawbone, and this invention is characterized by the following means, an artificial tooth, implant device with an arrangement where at least two implant bodies, each having a shaft portion, form a pair, a hook portion, hooked in a hook hole bored in a jawbone, is provided on the shaft portion of each implant body, the hook, portion is bent with respect to the shaft portion, and when the respective implant bodies are hooked onto the jawbone, tip portions of the hook portions are positioned so as to face (Continued)

each other inwardly, the arrangement being provided with a fixing means for fixing the implant bodies to each other.

15 Claims, 7 Drawing Sheets

(52) U.S. Cl.
CPC .......... *A61C 8/0043* (2013.01); *A61C 8/0045* (2013.01); *A61C 8/0027* (2013.01)

(56) References Cited

FOREIGN PATENT DOCUMENTS

| JP | 2007-75532 | 3/2007 |
|----|------------|--------|
| JP | 2010-63854 | 3/2010 |
| JP | 2012-34831 | 2/2012 |

\* cited by examiner

IMPLANTS FOR AN ARTIFICIAL TOOTH

FIELD OF THE INVENTION

The present invention relates to implants for an artificial tooth and specifically relates to an artificial tooth implant device using a plurality of implant bodies for a single tooth,

BACKGROUND AND DESCRIPTION OF RELATED ARTS

Dental implant treatment, performed upon loss of a natural tooth and by implanting an artificial tooth root (implant body) in the jawbone at the location of tooth loss and using the artificial tooth root as a base to mount an artificial tooth thereon, has been conventionally known.

With the dental implant treatment that is currently being practiced, after surgically excising the gum above the jawbone (alveolar bone), an implant body of a size determined beforehand by examination is implanted in the jawbone and thereafter, there is a necessary waiting period of three months to six months for integration (osseointegration) of the implant body and the jawbone. Treatment is then performed through the procedures of mounting a pedestal, referred to as an. "abutment body," on the implant body that has integrated with the jawbone and mounting an artificial tooth that has been molded to a predetermined size in advance on the abutment body.

The dental implant treatment is performed in accordance with these procedures and therefore six months to one year are generally required as a treatment, period.

Also, depending on the patient, the bone amount (especially the bone thickness) required for implanting the implant body may be insufficient, especially in the case of performing treatment on the maxilla. In this case, first, an auxiliary operation, such as a guided bone regeneration method (GBR method), ridge expansion, socket lifting, sinus lifting, etc., is performed on the jawbone and the dental implant treatment is performed upon forming the necessary bone amount, thus requiring an additional treatment period of several months.

As a dental implant treatment that does not require such an auxiliary operation, the art described in Patent Document 1 is proposed.

The art described in Patent Document 1 is: "A dental component implant having a composite structure that includes three leg implant bodies, implanted and fixed as tooth roots in the alveolar bone of a maxilla molar portion and forming a leg structure, a tooth root pedestal portion, provided with keeping holes of inner diameters greater than the outer diameters of the leg implant bodies to enable the leg implant bodies to be inserted movably and having a function of integrating the respective leg implant bodies inserted in the keeping holes, and an abutment, which is a supporting base coupled to the tooth root pedestal portion and on which a tooth crown is loaded."

In summary, the art is a dental component, implant having a composite structure with which there are three implant bodies that are implanted as tooth roots in the alveolar bone, the three implant bodies are integrated by the tooth root pedestal portion, and an abutment is added to these components.

The following effects are obtained by this art: "Implantation is possible regardless of the shape of the maxilla or the mandible or the position of the inferior alveolar nerve running at a lower portion of the mandible, and by the plurality of leg implant bodies supporting the tooth root pedestal portion, the occlusion load is dispersed among the respective leg implant bodies to prevent biased concentration of stress and the load is applied to a major axis direction of the abutment so that the life of the implant as a whole is elongated. Additional operation by the guided bone regeneration method for an increase of bone amount, etc., is thereby made unnecessary and application of implant implantation for cases of insufficient bone amount or cases unsuitable for implantation is made possible."

However, with the art described in Patent Document 1, although auxiliary operation by the guided bone regeneration method, etc., for cases of insufficient bone amount or cases unsuitable for implantation is made unnecessary, the period for integration of the implant bodies and the jawbone is still required and the problem that six months to one year are required as the treatment period still remains.

On the other hand, the arts described in Patent Document 2 are proposed in regard to a dental implant treatment that does not require a period for integration of the implant bodies and the jawbone.

An art described in Patent Document 2 is: "An artificial tooth fixture including a locking shaft, driven into an upper alveolar bone, which, among the alveolar bones, faces the oral cavity side, and an abutment having the locking shaft projecting integrally from a lower end and having an artificial tooth mounted, on an upper portion thereof." Further, "a locking shaft made up of a plurality of shafts, with each locking shaft having locking barb projections at a tip and a plurality of locations in a longitudinal direction of an outer periphery of the shaft," is also proposed.

The following effects are obtained by these arts: "An abutment can be mounted on an upper alveolar bone immediately without waiting for a period of several months for the integration of the implant material and the alveolar bone as in the conventional case." Further, "the locking shaft has locking barb projections at the tip and the plurality of locations in the longitudinal direction of the outer periphery of the shaft, and therefore the driving of the locking shaft into the alveolar bone can be facilitated and the force of binding of the abutment to the alveolar bone by the locking shaft can be made sufficiently high."

However, with the art described in patent Document 2, the locking shaft provided on the abutment cannot be fixed unless it is driven considerably deeply into the alveolar bone, and even, if barb projections are provided on the locking shaft, although the possibility of coming off is decreased, the locking shaft must be driven strongly into the alveolar bone using a hammer, etc., and there is thus the problem that not only is fixing insufficient but a large burden is also placed on the bone.

An art with the theme of lightening the burden on the bone has also been proposed.

The art described, in Patent Document, 3 is: "A dental implant with which a body portion of the implant is planted in a bone and a head portion of the implant is projected above the bone, the implant being arranged so that single surfaces of the respective head portions of two implants are clasped together and the body portions of the implants form a truncated chevron shape, the form of the character of 8 of a Japanese numeral, inside the bone in this state."

The following effects are obtained by this art: "An implant can be provided, with which initial fixing is secured without requiring expertise by removing just the necessary amount of bone at the location of planting of the implant and implanting the implant body easily without causing the implant to sink in more than necessary and with which the force applied to the implant in the vertical direction due to subsequent occlusal pressure is relaxed to prevent perturbation and sinking of the implant and increase the establishment of long-term functioning within the oral cavity."

However, with the art described in Patent Document 3, a specialized circular cutting tool must be used to dig a groove for planting the body portion of the implant. There is also the problem that the process of digging a groove in a jawbone is a process that a dentist, does not have experience in and is thus extremely difficult. Further, even with the art. a period for integration of the implant body and the jawbone is required and therefore a long period is still required as the treatment period.

Patent Documents

Patent Document 1: Japan Patent No. 4226609
Patent Document 2: Japan Patent Pre-Publication No. H8-196547
Patent Document 3: Japan Pre-Publication No. 2010-063854

SUMMARY OF THE INVENTION

Problems to be Solved by the Invention

Therefore, an object of the present invention is to provide an artificial tooth implant device that does not require a period for integration of implant bodies and a jawbone as in the background art, enables treatment even of a patient whose jawbone is small in bone amount or thickness, can reduce the treatment period and the number of times of treatment for many patients, and can lighten the mental and physical burden of a patient by minimizing the impact to the jawbone.

Means for Solving the Problems

The object of the present invention is achieved by the following-means.

1. An implant for artificial tooth with an arrangement where at least two implant bodies, each having a shaft portion, form a pair,
a hook portion, hooked in a hook hole bored in a jawbone, is provided on the shaft portion of each implant body,
the hook portion is bent with respect to the shaft portion, and
when the respective implant bodies are hooked onto the jawbone, tip portions of the hook portions are positioned so as to face each other inwardly,
the arrangement being provided with a fixing means for fixing the implant bodies to each other, 2. The implant for artificial tooth according to the above 1, where each hook portion has a doglegged shape.

3. The implant for artificial tooth according to the above 1 or 2, where each hook portion has a step portion provided between the tip portion and another portion and the tip portion is smaller in diameter than the other portion.

4. The implant for artificial tooth according to any one of the above 1 to 3, with an arrangement where the fixing means for fixing the implant bodies to each other is provided at the shaft portions of the implant bodies,
the fixing means has hole portions, to be put in communication respectively, in the shaft portions of the respective implant bodies and a fixing member inserted into the communicated hole portions, and
the shaft portions of the respective implant bodies are fixed to each other by the fixing means.

5. The implant for artificial tooth according to the above 4, with an arrangement having an abutment body that becomes a pedestal on which the artificial tooth is mounted, and
where a side surface hole portion is provided in a side surface of the abutment body such that the fixing member is inserted therein and in the hole portions, to be put in communication respectively, at the shaft portions of the respective implant, bodies, and
the shaft portions of a plurality of the implant bodies are fixed.

Effects of the Invention

With the invention according to the above 1, each implant body can be mounted on the jawbone by hooking the hook portion provided on the implant body in the hook hole bored in the jawbone. By this mounting means, the plurality of implant bodies are mounted onto the jawbone for a single tooth and the plurality of implant bodies are fixed to the jawbone by integrally integrating the implant, bodies.

The hook portion provided on each implant body is provided so as to be bent with respect to the shaft portion, for example, in a manner such that an end portion of the shaft portion is bent, and this hook portion is hooked in the hook hole bored in the direction of being bent similarly with respect to the direction of the shaft portion and therefore does not come off in the shaft portion direction. Further, the respective implant bodies are arranged so that in being hooked onto the jawbone, the implant bodies are positioned to face each other so the directions of bending of the hook portions are mutually directed inwardly. By integrally integrating the respective implant bodies, the implant bodies are not only prevented from coming off in the directions of bending of the hook portions but can also be fastened, so as to clamp the jawbone and be fixed extremely firmly.

Unlike the conventional implant treatment, the implant bodies are not implanted deeply by being screwed into the jawbone, etc., but have the arrangement where the hook portions are booked in the hook holes bored shallowly in the jawbone and thus enable treatment without having to perform an auxiliary operation, etc., even when the bone amount or thickness of the jawbone is small. Also, impacts, such as injury, etc., to the jawbone due to deeply implanting the implant bodies can be minimized.

With the implant for artificial tooth of the above arrangement, by simply hooking the implant bodies onto the jawbone and integrally integrating the respective implant, bodies, the integrally integrated implant bodies are fixed to the jawbone, and therefore a period for integration of the implant bodies and the jawbone is not required, as in the conventional implant treatment and the treatment period and the number of times of treatment can be reduced. Treatment of a patient whose jawbone is small, in bone amount or thickness is also enabled, and elongation of the treatment period due to an auxiliary operation can also be avoided.

Further, each hook portion can be formed to a thinness approximate to that of an injection needle, each hook hole can be provided in the jawbone with a dental drill of similar thinness, and the hook portion of the implant body can be mounted in the book hole, and therefore treatment is possible without having to peel off the gum covering the jawbone and bleeding of the gum can be suppressed to the minimum. The treatment time can thereby be reduced and firm fixing can be achieved while minimizing damage to the jawbone and the gum.

That is, the implant for artificial tooth according to the present invention differs fundamentally from the conventional implant treatment in which the implant bodies are fused to the jawbone, and an artificial tooth implant device can thus be provided with which firm fixing by a mode of clamping by two implant bodies can be achieved while reducing the treatment period and the number of times of treatment of many patients regardless of the bone amount of the jawbone, etc., and minimizing the impact to the jawbone to lighten the mental and physical burden of the patients.

With the invention according to the above 2, the hook portion of each implant body is formed into the doglegged shape to enable two or more shaft portions to be positioned and fixed upon being brought close together.

The implant for artificial tooth according to the present, invention has the arrangement where the tip portions of the hook portions are positioned so as to face each other inwardly, and therefore to position the respective tip portions of the hook portions so as not to contact each other, the respective shaft portions are positioned apart by a considerable distance. However, by making the hook portion of each implant, body have the doglegged shape, an upper portion of the doglegged shape is bent in an outward direction with respect to the other implant body and therefore the tip portion positioned at a lower portion of the doglegged shape can be positioned close to an axial direction extension line of the shaft portion. The respective implant bodies can thereby be positioned with the shaft portions being brought close to each other and these shaft portions can also be fixed, easily.

Also, the upper portion of the doglegged shape, "<", is interposed between the portion made to penetrate into the jawbone (a portion of the lower portion of the doglegged shape,) and the shaft portion so that a gap is provided at a portion corresponding to the position, immediately below the shaft, portion to enable the implant body to be prevented or suppressed from compressing the gum at this location and enable the blood circulation in the gum at this location to be maintained. Impacts to the entire oral cavity including the gum can thereby be minimized.

With the invention according to the above 3, the step portion is provided between the tip portion and the other portion of each hook portion and the tip portion is formed to a smaller diameter than the other portion so that the depth of penetration of the hook portion into the hook hole can be made fixed. To describe specifically, first, in regard to the hook hole provided, in the jawbone, the jawbone is bored with a guide drill of substantially the same diameter as the tip portion of the hook, portion and a portion of the hole is enlarged in diameter by an implant drill of substantially the same diameter as the portion besides the tip portion to form the hook hole with diameters of two stages. When the hook portion is thereafter inserted in the hook hole bored to have the diameters of two stages, the penetration of the hook portion into the hook hole is stopped by contact of the step portion of the hook hole with the step portion of the hook portion to enable the depth of penetration of the hook portion into the hook hole to be made fixed. The depth of penetration of the hook portion can be adjusted by the depth to which the enlargement of diameter by the implant drill is performed.

Also, the penetration depth of the hook portion can be kept fixed and this in combination with the doglegged shape of the hook portion in 2 above results in the provision of a gap at a portion corresponding to a position immediately below the shaft portion so that the gum at this location is prevented from being compressed by the implant body and the blood circulation n in the gum at this location can be maintained. Impacts to the entire oral, cavity including the gum can thereby be minimized.

With the invention according to the above 4, the arrangement, where the hole portions, to be put in communication respectively, are provided in the respective shaft portions of two implant bodies and the two shaft portions are fixed by inserting the fixing member into the communicated hole portions after the shaft portions have been positioned, is adopted as the fixing means for fixing the two implant bodies. It therefore suffices to provide just the hole portions in the respective shaft portions so that processing is easy, and also in fixing the shaft portions of the two implant bodies, it suffices to simply insert the fixing member in the communicated hole portions so that secure fixing is enabled even though the treatment is simple.

With the invention according to the above 5, the hole portions provided in the shaft portions of the implant bodies and the side surface hole portion provided in the side surface of the abutment body are put in communication by the fixing member so that the plurality of the implant bodies and the abutment body can be fixed integrally.

MODE(S) FOR CARRYING OUT THE INVENTION

Unlike dental implant treatments that are currently being practiced, an artificial tooth implant device 1 according to the present invention does not require integration (osseointegration) of implant bodies and a jawbone after implanting of the implant bodies into the jawbone and is an artificial tooth implant device that can reduce the treatment period and the number of times of treatment.

The present invention shall now be described in detail in accordance with the attached drawings.

Figure 1:
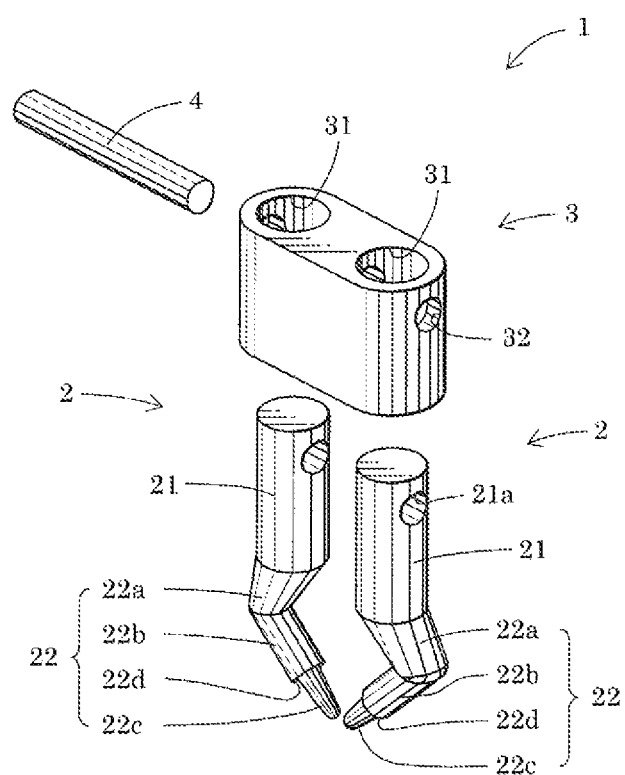
FIG. 1 is a schematic perspective view of an embodiment of the present invention.
Figure 2:
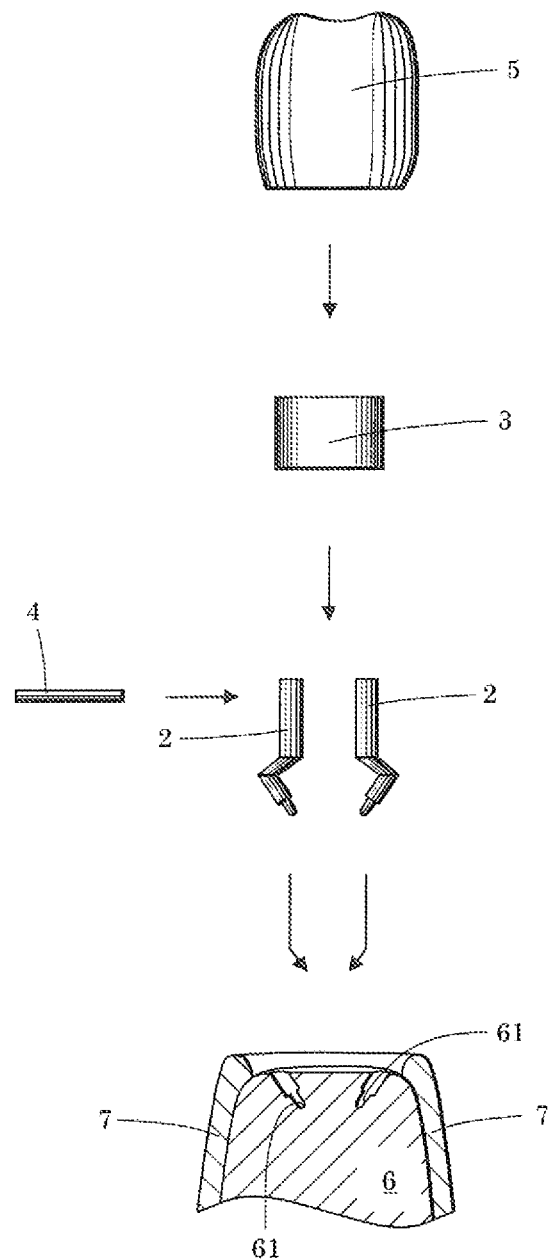
FIG. 2 is a schematic view showing decomposed elements of the embodiment of the present invention

FIG. 1 is a schematic perspective view of an embodiment of the artificial tooth implant device I according to the present invention (may hereinafter be referred to simply as "artificial tooth implant device"), and FIG. 2 is a schematic view showing decomposed elements of the embodiment of the artificial tooth implant device 1 of the present invention.

As shown in FIG. 1, the artificial tooth implant device 1 is made up of at least two implant bodies 2 and may have an arrangement with an abutment body 3 and a fixing member 4 added thereto. An artificial tooth 5 is mounted on the implant bodies 2 directly or via the abutment body 3.

The implant bodies 2 in the present invention are arranged to be fixed by being hooked in hook holes 61 provided in a jawbone 6, which, in particular, is an alveolar bone.

As shown in FIG. 1, each implant body 2 is arranged from at least a shaft portion 21 and a hook portion 22.

The shaft portion 21 is erected in the same direction as the direction in which a natural tooth grows from the jawbone 6 and is a portion at which the jawbone 6 and the artificial tooth 5 are connected and fixed directly or via the abutment body 3 to be described, below.

The shaft portion 21 is not restricted in shape and may, for example, be formed into a cylindrical shape as shown in FIG. 1.

Although the shaft portion 21 is not restricted in size, when it is formed, for example, to a cylindrical shape as shown in FIG. 1, it is preferably formed to have a length of 5 mm to 15 mm and a diameter of 0.5 mm to 3 mm, and in regard, to the diameter, forming to a diameter of 0.7 mm to 1.5 mm is more preferable.

In regard to the size, such as the length and diameter, the shaft portion 21 may be processed by a dentist in accordance with the patient in the actual situation of treatment. In particular, the size and shape may be processed by trimming with a dental drill, etc., and therefore the implant body 2 is preferably slightly larger than the required size.

As shown in FIG. 1, a hole portion 21a, penetrating through in a direction orthogonal, to an axial direction, is provided in a side surface of each shaft portion 21.

The hole portions 21a are formed so as to communicate in the shaft portions 21 of a plurality of implant bodies 2 that are used together, and the shaft portions 21 of the plurality of implant bodies 2 can be fixed by inserting a rod-shaped fixing member 4 (to be described later) through the respective hole portions 21 in a bolt-like manner.

The hook portion 22 is provided at the jawbone 6 side of the shaft portion 21 and is a portion that is hooked in a hook hole 61 bored in the jawbone 6. In other words, the hook portion 22 is a portion that penetrates shallowly into and latches in the hook hole 61 that is bored at an angle bent from the axial direction of the shaft portion 21.

As shown in FIG. 1, the hook portion 22 is provided at an end portion at the jawbone 6 side of the shaft portion 21, is provided in a direction that is bent with respect to the axial direction of the shaft portion 21 and is formed into a column-like, rod-like, tapered, or needle-like form.

The hook portion 22 is provided so as to be bent with respect to the shaft portion 21, for example, by bending an end portion of the shaft portion 21, and the hook portion 22 is penetrated into and hooked in the hook hole 61, bored in the direction that is similarly bent with respect to the direction of the shaft portion 21, so as not to come off in the axial direction of the shaft, portion 21. Further, the respective implant bodies 2 are mounted so that tip portions 22c of the hook portions 22 face each other inwardly and the implant bodies 2 are integrated integrally so as not to come off in the bend direction of the hook portion 22 either.

As the shape of the hook portion 22, a doglegged shape, "<", may be adopted as shown in FIG. 1. When the hook portion 22 is made to have the doglegged shape, its shaft portion 21 side is referred to as an "upper portion 22a" and a portion bent in the opposite direction from the upper portion 22a is referred to as a "lower portion 22b." Also, an end portion of the lower portion 22b is referred to as a "tip portion 22c" of the hook portion 22. In relation to the shape of the hook hole 61 to be described below, the portion of the lower portion 22b besides the tip portion 22c preferably has a cylindrical shape and, on the other hand, the tip portion 22c preferably has a tapered cylindrical shape or a needle-like shape.

Although in FIG. 1, the upper portion 22a and the lower portion 22b are illustrated as being substantially equal, in length, the lengths of these portions are not restricted and an arrangement in which one is longer than the other is also possible.

In FIG. 1, the angle between the upper portion 22a and the lower portion 22b is illustrated as being substantially 90 degrees and although this angle is not restricted, it is preferably within a range of 30 degrees to 150 degrees and more preferably within a range of 60 degrees to 120 degrees.

Also, in regard to bend angles with respect to the shaft portion 21, although those of the upper portion 22a and the lower portion 22b are respectively illustrated as being approximately 45 degrees in FIG. 1, these angles are also not restricted and, for example, an arrangement may be adopted where the upper portion 22a is bent at 30 degrees with respect to the shaft portion 21, the lower portion 22b is bent at 60 degrees with respect to the shaft portion 21, and the angle between the upper portion 22a and the lower portion 22b is formed to be 90 degrees.

An arrangement is also possible where the bend angle of the hook portion 22 with respect to the shaft portion 21 can be adjusted by curving of the upper portion 22a or the lower portion 22b or both of these portions of the hook portion 22. In this case, even if the bend angle (with respect to the shaft portion 21) of the hook portion 22 is not matched with the angle (with respect to the shaft portion 21) of the hook hole 61 bored in the jawbone, a dentist can adjust the bend angle of the hook portion 22 and make it match the angle of the hook hole 61 in the actual clinical situation. As means for curving of the hook portion 22, application of force using dental pliers, etc., or making the hook portion 22 easily curvable by heating, etc., may be cited.

Also, to maintain strength, the hook portion 22 may have an arrangement that cannot be curved. In this case, a plurality of implant bodies 2 that differ in the curve angle of the hook portion 22 may be prepared in advance and that which matches the angle of the hook hole 61 may be selected and used.

Figure 3:
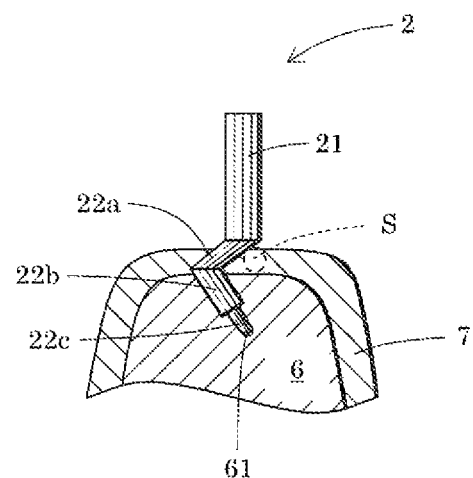
FIG. 3 is a schematic explanatory diagram of the positioning of a hook portion of an implant body, a gum, and a jawbone.

Effects of forming the hook portion 22 to have the dog-legged shape, "<", shall now be described in accordance with FIG. 3.

The artificial tooth implant device 1 has the arrangement where the tip portions 22c of the hook portions 22 are positioned so as to face each other inwardly, and therefore to position the respective tip portions 22c of the hook portions 22 so as not to contact each other, the respective shaft portions 21 are positioned apart by a considerable distance. However, by making the hook portion 22 of each implant body 2 have the doglegged shape, the upper portion 22a of the doglegged shape is bent in an outward, direction with respect to the other implant body 2 and therefore the tip portion 22c positioned at the lower portion 22 of the doglegged shape, "<", can be positioned close to an axial direction extension line of the shaft portion 21. The respective implant bodies 2 can thereby be positioned with the shaft portions 21 being brought close to each other and these shaft portions 21 can also be fixed easily.

Also, the upper portion 22a of the doglegged shape, "<", is interposed between the tip portion 22c of the hook portion 22 that is made to penetrate into the jawbone 6 and the shaft, portion 21 so that a gap S is provided at a portion between the shaft portion 21 and the jawbone 6 and corresponding to the position immediately below the shaft portion 21 to enable the implant body 2 to be prevented or suppressed from compressing a gum 7 at this location and enable the blood circulation in the gum 7 at this location to be maintained. Impacts to the entire oral cavity including the gum 7 can thereby be minimized.

Preferably, the hook portion 22 has a step portion 22d provided between the tip portion 22c and the other portion and the tip portion 22c is smaller in diameter than the other portion. This arrangement shall now be described in accordance with FIG. 4.

Figure 4:
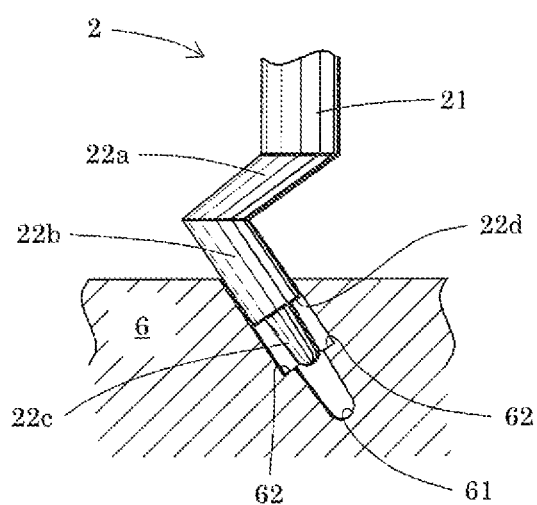
FIG. 4 is a schematic explanatory diagram illustrating an effect due to the provision of a step portion in the hook portion of the implant body.

The arrangement in FIG. 4 is an example where the hook portion 22 is made to the doglegged shape and therefore the tip portion 22c is positioned at the lower portion 22b of the hook portion 22 and the step portion 22d is provided at the lower portion 22b.

By providing the hook portion 22 with the step portion 22d and making the tip portion 22c have a smaller diameter than the other portion, the depth of penetration into the hook hole 61, bored in the jawbone 6, can be made fixed. To describe specifically, first, in regard to the hook hole 61 provided in the jawbone 6, the jawbone 6 is bored with a dental drill (for example, a guide drill) of substantially the same diameter as the tip portion 22c of the hook portion 22 and a portion of the hole is enlarged in diameter by a dental drill (for example, an implant drill) of substantially the same diameter as the portion besides the tip portion to form the hook hole 61 with diameters of two stages. The step provided in the hook hole 61 is referred, to as a "hook hole step portion 62." When the hook portion. 22 is thereafter inserted in the hook hole 61 provided with the hook hole step portion 62, the penetration of the hook portion 22 info the hook hole 61 is stopped by contact of the hook hole step portion 62 with the step portion 22d of the hook portion 22 to enable the depth of penetration of the hook portion 22 into the hook hole 61 to be made fixed. The depth of penetration of the hook portion 22 can be adjusted by the depth to which the enlargement of diameter by the implant drill or other dental drill is performed, that is, by the depth position of the hook hole 61 at which the hook hole step portion 62 is provided.

Also, the penetration depth of the hook portion 22 can be kept fixed and this In combination with the effect of the hook portion being made to have the doglegged shape results in the provision of the gap S at the portion corresponding to the position immediately below the shaft portion 21 (see FIG. 3) so that the gum 7 at this location is prevented from being compressed by the implant body 2, the blood circulation in the gum 7 at this location can be maintained, and impacts to the entire oral cavity including the gum 7 can thereby be minimized.

Although the hook portion 22 is not restricted in size, in weighing the required strength and impacts to the jawbone, it is preferable for the length to be 2 mm to 8 mm, the diameter to be no more than 2.5 mm, and in regard to the diameter, forming to no more than 2.0 mm is preferable, to no more than 1.5 mm is especially preferable, and to no more than 1.0 mm is preferable above all. Also, in the arrangement in which the step portion 22d is provided in the hook portion 22, it is preferable for the diameter of the tip portion 22c to be no less than 0.1 mm smaller than that of the other portion. An arrangement with a small diameter is suitable for treatment of a front tooth or upper jaw, and an arrangement with a large diameter is suitable for treatment of a back tooth or lower jaw. In regard to the length and diameter of the hook portion 22, a dentist may perform processing in accordance with the patient in the actual situation of treatment.

The hook portion 22 can be made to have an extremely small size with a diameter approximate to that of an injection needle (for example as mentioned above, a maximum diameter of no more than 2.5 mm, preferably no more than 2.0 mm, especially preferably no more than 1.5 mm, and above all preferably no more than 1.0 mm) and a length of approximately 5 mm so that treatment can be performed from above the gum 7 without cutting the gum 7 and the implant bodies 2 can be mounted on the jawbone 6 from outer sides of the gum to enable lightening of the physical and mental pain and burden of a patient.

Also, although the bend angle of the hook portion 22 with respect to the shaft portion 21 (the bend angle of the lower portion 22b with respect to the shaft portion 21 in the case where the hook portion 22 has the doglegged shape) is not restricted, it is preferably within the range of 10 degrees to 60 degrees and more preferably within the range of 30 degrees to 50 degrees. When the bend angle is small, there is a possibility of the implant body 2 coming off in the axial direction, and when the bend angle is large, the thickness of the jawbone 6 covering the hook portion 22 (or the hook hole 61) from above is thin so that there is a possibility of this portion cracking when a strong force is applied and it is also difficult to mount the hook portion 21 and bore the hook hole 61.

The respective portions making up the implant body 2 are preferably formed integrally using a material having adequate strength and hardness. There are no restrictions in the material used, materials that are publicly known and publicly used as materials for implant bodies may be adopted without any restrictions in particular, and besides a metal, such as titanium or an alloy thereof, ceramics, zirconia, etc., may be cited as examples.

Next, the abutment body 3 shall now be described.

The abutment body 3 becomes a pedestal, which fixes the shaft portions 21 of a plurality of implant bodies 2 and on which the artificial tooth 5 is mounted.

As shown in FIG. 1, the abutment body 3 is provided with shaft portion insertion hole portions 31 of a number that is in accordance with the number of the implant bodies 2. Each shaft portion insertion hole portion 31 is in accordance with the shape of the shaft portion 21 of the corresponding implant body 2 and the respective shaft portions 21 of the implant bodies 2 are inserted into the respective shaft portion insertion hole portions 31. By making the shapes of the shaft portion insertion hole portions 31 match with the shapes of the shaft portions 21 in advance, the plurality of implant bodies 2 are integrated or fixed by the respective shaft portions 21 being inserted in the shaft portion insertion hole portions 31.

Although FIG. 1 shows an arrangement where two implant bodies 2 are inserted, in a case where three implant bodies 2 are inserted, three shaft portion insertion hole portions 31 are provided, and in a case where four implant bodies 2 are inserted, four shaft portion insertion hole portions 31 are provided. Each shaft portion insertion hole portion 31 may be formed to be slightly larger than the shaft portion 21 to be inserted and a gap that forms with respect to the shaft portion 21 may be filled with dental cement, etc., in use. Also, although with the mode shown in FIG. 1, the holes penetrate through from a plane surface to a bottom surface, a mode with bottomed holes that are closed at the plane surface side may be adopted instead (not shown).

Besides the mode illustrated in FIG. 1, the abutment body 3 may be formed to have a hollow prismatic shape (not shown). In this case, the shaft portions 21 of the plurality of implant bodies 2 are inserted in the hollow portion. By making the shape of the hollow portion 31a match with the shape of the shaft portions 21 of any number of implant bodies 2 in advance, the plurality of shaft portions 21 inserted in the hollow portion are housed tightly inside the hollow portion and are integrated or fixed in a bundled mode. Also, the hollow portion may be formed to be slightly larger than the shaft portions 21 to be inserted and a gap that forms with respect to the shaft portions 21 may be filled with dental cement, etc., in use.

As shown in FIG. 1, a side surface hole portion 32 that penetrates through in a direction orthogonal to the shaft portion insertion hole portions 31 is provided in side surfaces of the abutment body 3.

The side surface hole portion 32 is formed to be in communication with the hole portions 21a provided in the shaft portions 21 of the implant bodies 2 put in communication with the shaft portion insertion hole portions 31, and the shaft portions 21 of the plurality of implant bodies 2 and the abutment body 3 can be fixed by inserting the rod-shaped fixing member 4 (to be described later) in a bolt-like manner in the respective hole portions 21 and the side surface hole portion 32.

Figure 5:
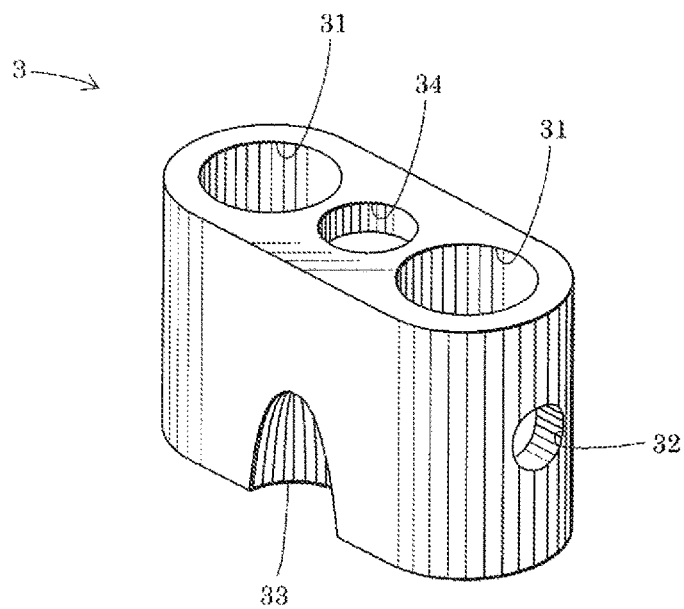
FIG. 5 is a schematic perspective view of an abutment body provided with side surface groove portions and a latching hole portion.

Mutually opposite side surface groove portions 33 may be provided in side surfaces of the abutment body 3 as shown in FIG. 5 (the other side surface groove portion 33 formed at the rear side surface in the figure is not illustrated). By providing the side surface groove portions 33, the gum 7 in the periphery can be made to gradually enter the side surface groove portions 33 after the mounting of the abutment body 3 on the implant bodies 2 installed in the jawbone 6 to fortify the adhesion of the abutment body 3 and the gum 1. Also, blood circulation in the gum 7 can be secured by increasing the amount of the gum 7 enveloping the abutment body 3.

Each side surface groove portion 33 preferably has, for example, a shape of an incliningly cut groove that gradually becomes shallow in depth toward a latching hole portion 34 to be described below.

The side surface groove portion 33 may be provided in the side surface at just one side or one each may be provided at each of mutually opposite side surfaces as described above or, further, a plurality may be provided at one or each of both side surfaces.

As shown in FIG. 5, the latching hole portion 34 may be provided in the plane surface (the surface positioned at the opposite side with respect to the jawbone 6 when mounting on the implant bodies 2) of the abutment-body 3. The latching hole portion 34 may be used to mount another member and, for example, if the height of the abutment body 3 is to be extended, an extension member may be mounted or use may be made in mounting the artificial tooth 5.

The latching hole portion 34 is preferably provided at a depth not penetrating through to the side surface hole portion 32. Also, a female thread (not shown) may be provided in the latching hole portion 34.

The abutment body 3 is preferably formed integrally using a material having adequate strength and hardness. There are no restrictions in the material used, materials that are publicly known and publicly used as materials for an abutment body may be adopted without any restrictions in particular, and besides a metal, such as titanium or an alloy thereof, ceramics, zirconia, etc., may be cited as examples.

With the present invention, even if the strength necessary for fixing the artificial tooth 5 to the jawbone 6 cannot be obtained with just the implant bodies 2, the necessary and sufficient strength can be obtained by integrating the abutment body 3 with the plurality of implant bodies 2.

The fixing member 4 shown in FIG. 1 is arranged to be inserted in a bolt-like manner through the hole portions 21a respectively provided in the shaft portions 21 of the plurality of implant bodies 2 to fix the plurality of implant bodies 2 in one piece. Also, the fixing member 4 is arranged to be inserted in a bolt-like manner through the hole portions 21a respectively provided in the shaft portions 21 of the plurality of implant bodies 2 and the side surface hole portion 32 provided in the abutment body 3 to fix the plurality of implant bodies 2 and the abutment body 3.

As a means for fixing the plurality of implant bodies 2, a means may be cited with which the fixing member 4 is inserted in a bolt-like manner through the hole portions 21a provided in the shaft portions 21 of the respective implant bodies 2. To prevent the fixing member 4 from coming off from the hole portions 21a, the periphery of the member is preferably hardened with dental cement, etc., after insertion. A means with which the abutment body 3 is capped onto the shaft portions 21 of the plurality of implant bodies 2 may also be cited. Further, a means combining the above means where the abutment body 3 is capped onto the shaft portions 21 of the implant bodies 2 and the fixing member 4 is inserted in a bolt-like manner through the hole portions 21a and the side surface hole portion 32 that are communicatingly provided in the shaft portions 21 and the abutment body 3 may also be cited.

The means for fixing the plurality of implant bodies 2 does not have to use the fixing member 4 and may implement fixing by adhesion using dental cement, etc., instead.

The fixing member 4 is not restricted in shape and may, for example, be formed into a cylinder, such as shown in FIG. 1, or other rod-like body.

The fixing member 4 is preferably formed integrally using a material having adequate strength and hardness. There are no restrictions in the material used, and as with the materials of the implant bodies and the abutment body, materials that are publicly known and publicly used may be adopted without any restrictions in particular, and besides a metal, such as titanium or an alloy thereof, ceramics, zirconia, etc., may be cited as examples.

With the present invention, at least two implant bodies 2 are used. Although two implant, bodies 2 are used in the embodiment illustrated in FIG. 1, three or more implant bodies 2 may be used per tooth, and particularly at a location, such as at a back tooth, where there is a sufficient bone amount in the jawbone 6 and strength is required, four to six implant bodies 2 may be used.

An embodiment where four implant bodies 2 are used for one tooth shall now be described in accordance with FIG. 6.

Figure 6:
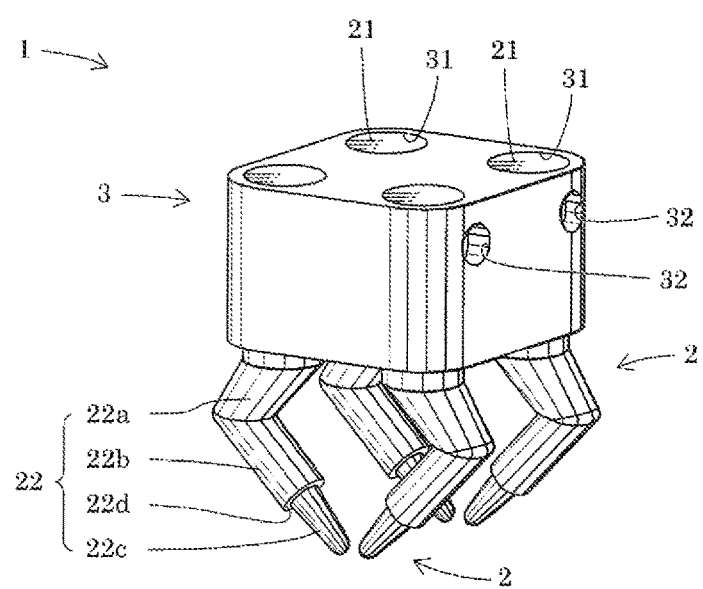
FIG. 6 is a schematic perspective view of an embodiment using four implant bodies.

With the implant bodies 2, two implant bodies 2, positioned so that the tip portions 22c of the respective hook portions 22 face each other inwardly, are used as a pair and two such pairs are aligned as shown in FIG. 6.

As the abutment body 3, that provided with four shaft portion insertion hole portions 31 is used and one shaft portion 21 is inserted in each shaft, portion insertion hole portion 31. Two sets of the side surface hole portions 32 penetrating through in a direction orthogonal to the shaft portion insertion hole portions 31 are provided.

Two fixing members 4 (omitted from illustration in FIG. 6) are used. After mounting the abutment body 3 on the four implant bodies 2, a single fixing member 4 is inserted through, the hole portions 21a of two implant bodies 2 and side surface hole portions 32 of the abutment body 3. Similarly, a single fixing member 4 is inserted continuously through the hole portions 21a of the other two implant bodies 2 and the other side surface hole portions 32 of the abutment body 3. The four implant bodies 2 and the single abutment body 3 are thereby fixed by the two fixing members 4.

Figure 7:
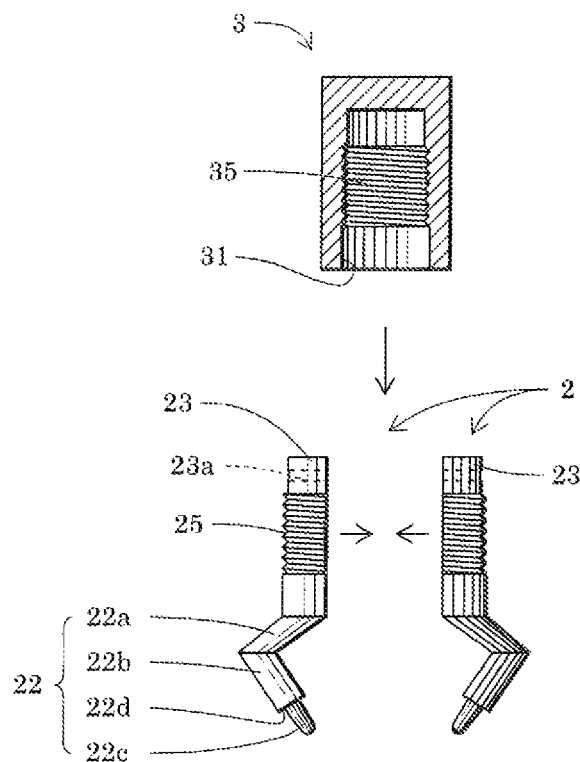
FIG. 7 is a partially sectional front view of another embodiment of the present invention.
Figure 8:
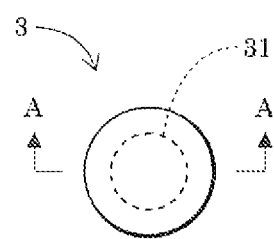
FIG. 8 is a plan view of an abutment body in FIG. 7.
Figure 9:
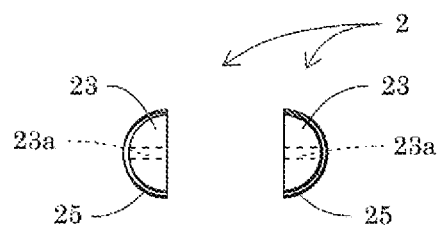
FIG. 9 is a plan view of implant bodies in FIG. 7 with hook portions being omitted.
Figure 10:
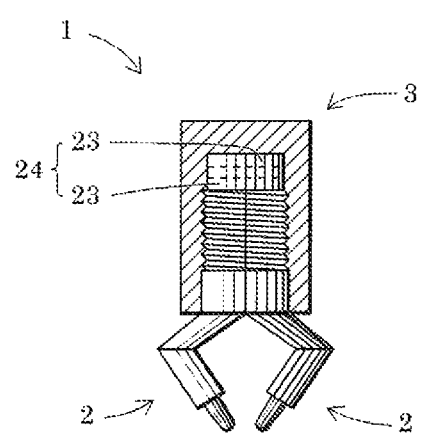
FIG. 10 is a partially sectional front view of the other embodiment of the present invention.
Figure 11:
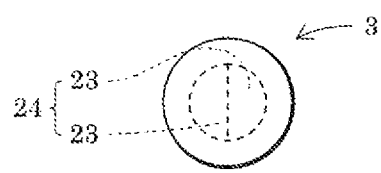
FIG. 11 is a plan view of an artificial tooth implant device shown in FIG. 10 with the hook portions of the implant bodies being omitted.

FIG. 7 to FIG. 11 show another embodiment of the present invention. FIG. 7 shows a sectional view taken along A-A of the abutment body 3 and a front view of the implant bodies 2. FIG. 8 is a plan view of the abutment body 3 in FIG, 7, and FIG. 9 is a plan view of the implant bodies 2 in FIG. 7 with the hook portions 22 being omitted. FIG. 10 is a partially sectional front view of the artificial tooth implant device 1 formed by integrating and fixing the implant bodies 2 and the abutment body 3 in FIG. 7. FIG. 11 is a plan view of the artificial tooth implant device 1 in FIG. 10 with the hook portions 22 being omitted.

The embodiment shown in FIG. 7 to FIG. 11 has an arrangement where the shaft portion of each implant body 2 is formed into a divided cylindrical shape (this shaft body is referred to as a "divided cylindrical shaft portion 23"), and the divided cylindrical shaft portions 23 of the two implant bodies 2 are joined to form a single joined cylindrical shaft portion 24. To describe specifically, the arrangement is such that the divided cylindrical shaft portion 23 of each implant body 2 is formed into the divided cylindrical shape, which is a shape resulting from dividing a cylinder in an axial direction and a single cylinder (joined cylindrical shaft portion 24) is formed when the two divided cylindrical shaft portions 23 are joined, and a single shaft portion of cylindrical shape can be formed by the joining of the two implant bodies 2.

By the joined cylindrical shaft portion 24 being formed as a single cylinder, the abutment body 3 and the artificial tooth 5 that cover it are made easy to process and mount, (fix) to enable a reduction, in production cost of the abutment body 3, etc., and shortening of the treatment time.

The embodiment shown in FIG. 7 to FIG. 11 has the arrangement where, in order to latch the divided cylindrical shaft portions 23 of the two implant bodies 2, hole portions 23a, which are to be put in communication, are provided respectively in the two divided cylindrical shaft portions 23, and the divided cylindrical shaft portions 23 of the two implant bodies 2 are latched by inserting the fixing member 4 (not shown in FIG. 7 to FIG. 13) through the communicated hole portions 23a after the two divided cylindrical shaft portions 23 have been joined. This arrangement is the same as that of the embodiment shown in FIG. 1.

As another means for latching the divided cylindrical shaft portions 23 of the two implant bodies 2, an arrangement may be cited, where a latching portion (not shown), such as a projecting portion, etc., is provided on the divided cylindrical shaft portion 23 of one of the implant bodies 2, a latched portion (not shown), such as a recessed portion, etc., is provided, on the divided cylindrical shaft portion 23 of the other implant body 2, and the divided cylindrical shaft portions 23 of the two implant bodies 2 are latched by latching or fitting, etc., of the latching portion and the latched portion to form the joined cylindrical shaft portion 24.

Also, the embodiment shown in FIG. 7 to FIG. 11 has an arrangement where a male thread 25 is provided on an outer periphery of the joined cylindrical shaft portion 24 and a female thread portion. 35, corresponding to the male thread 25 provided on the outer periphery of the joined cylindrical, shaft portion 24, is provided in the abutment body 3. With this arrangement, the abutment body 3 can be integrated by screwing and thereby fixed securely onto the joined cylindrical shaft portion 24 of the implant bodies 2. Although with the abutment body 3 shown in FIG. 7, etc., the shaft portion insertion hole portion 31 is illustrated as a bottomed hole, it may take on the form of a hole that penetrates through, from the plane surface to the bottom surface instead.

The artificial tooth implant device 1 may be applied to a full denture.

Figure 12:
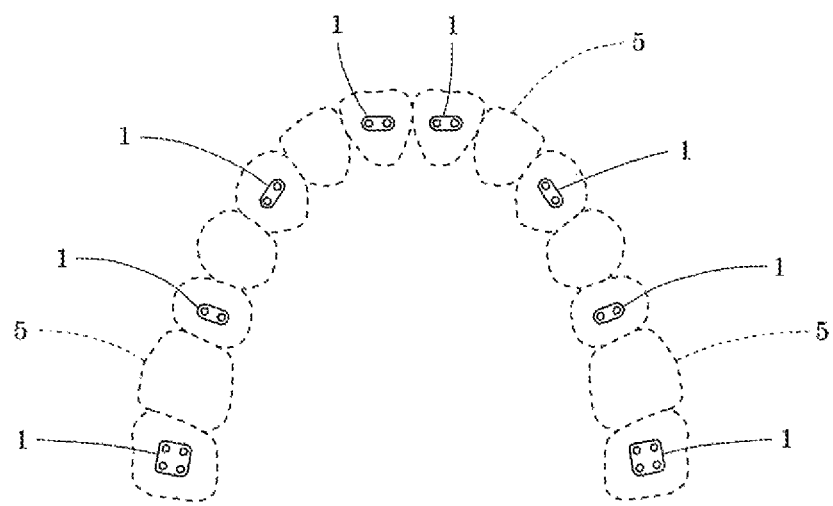
FIG. 12 is a schematic explanatory diagram of an example of application of the present invention to a full denture.

As shown in FIG. 12, by mounting sets, each of at least two paired implant bodies 2 and the abutment body 3, at suitable intervals on the jawbone 6 and mounting thereon connected artificial teeth 5 from a back tooth at one side to a back tooth at another side, the artificial tooth implant devices 1 can be used in the manner of a fill denture. Although indication of teeth corresponding to the third molars (wisdom teeth) is omitted in FIG. 12, the artificial tooth, implant devices 1 may also be mounted at positions corresponding to the third molars.

The artificial tooth implant device 1 may also be applied to a partial denture or a dental bridge.

Figure 13:
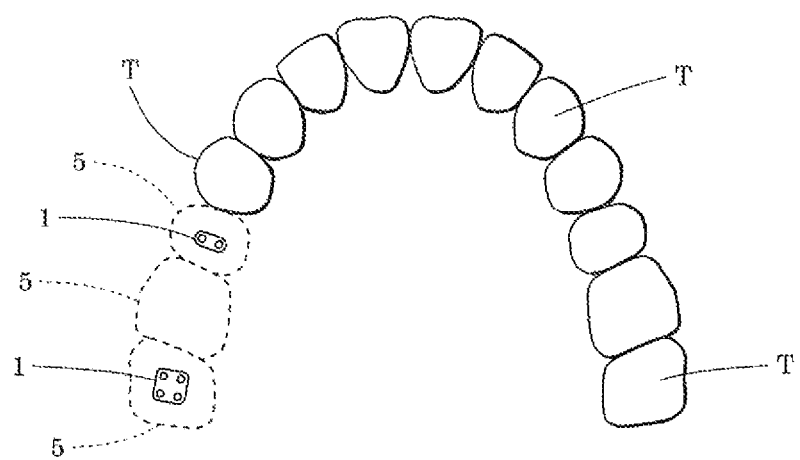
FIG. 13 is a schematic explanatory diagram of an example of application of the present invention to a dental bridge.

As shown in FIG. 13, by mounting sets, each of at least two paired implant bodies 2 and the abutment body 3, at respective ends of the jawbone 6 at a location where natural teeth were lost and mounting thereon connected artificial teeth 5 corresponding to the lost teeth, the artificial tooth implant devices 1 can be used in the manner of a partial denture or a dental bridge. Although indication of teeth corresponding to the third molars (wisdom teeth) is omitted in. FIG. 13, the artificial tooth implant devices 1 may also be mounted at positions corresponding to the third molars.

Treatment, procedure using the artificial tooth implant device 1 shall now be described.

Here, the procedures in a case of using two implant bodies 2, one abutment body 3, and one fixing member 4 as shown in FIG. 1 shall be described.

First, two hook holes 61 are bored in the alveolar bone of the jawbone 6 using a dental drill. In this process, the hook holes 61 may be bored upon cutting the gum 7 covering the jawbone 6 and exposing the jawbone 6 or it is also possible to bore the hook holes 61 in the jawbone 6 without cutting the gum 7, by inserting the dental drill in a puncturing mariner from above the gum 7. The hook portion 22 of each, implant body 2, with a diameter of no more than 3 mm, is an extra-fine member similar to an injection needle and it suffices that holes of substantially equal diameter be bored as the hook holes 61 so that it is possible to insert the dental drill in a puncturing manner in the gum 7 to reach the jawbone 6 to bore the hook holes 61 without cutting the gum 7.

As shown in FIG. 1, the two hook holes 61 are bored in mutually opposite directions that face each other inwardly and are preferably bored from an outer side toward an inner side of a tooth row or from an inner side toward an outer side of a tooth row. This is because when boring is performed from an inner side toward an outer side of a tooth row or in the opposite direction, adjacent teeth are not obstacles and the process is easy.

The hook holes 6.1 are preferably bored at angles substantially equal to the bend angles of the hook portions 22 in the implant bodies 2. If the gum 7 Is cut each hook hole 61 can be bored at any angle easily by providing a recess of spherical crown shape, etc., on a surface of the alveolar bone of the jawbone 6 before boring the hook, hole 61.

To specifically describe a means for boring each hook hole 61, first, the jawbone 6 is bored, using a guide drill of substantially the same diameter as the tip portion 22c of the hook portion 22 and a portion of the bored hole is enlarged in diameter using an implant drill of substantially the same diameter as the portion besides the tip portion 22c to form the hook hole 61 with diameters of two stages having the hole step portion 62. With the guide drill, it is preferable to bore to a depth approximately equal to or a depth no less than the length of the lower portion 22b of the hook portion 22, and with the implant drill, it is preferable to enlarge the diameter to a depth approximately equal to or a depth no more than the length of the portion of the lower portion 22b besides the tip portion 22c.

Thereafter, the hook portion 22 of the implant body 2 is inserted and hookingly mounted in one of the hook holes 61. As insertion is performed, the step portion 22d of the hook, portion 22 contacts the hook hole step portion 62 of the hook hole 61 and insertion to a further depth is prevented (see FIG. 4).

In this process, the implant body 2, with which the bend angle of the hook portion 22 matches the curve angle of the hook hole 61, is selected and used in accordance with the bend angle of the hook hole 61. In the case of the arrangement where the hook portion 22 of the implant body 2 is curvable, the hook portion 22 may be used upon being curved to match the bend angle of the hook hole 61.

Thereafter, the hook portion 22 of the implant body 2 is similarly mounted in the other hook hole 61 as well.

Here, with the two implant bodies 2, the respective shaft, portions 21 approach each other so as to be drawn together mutually in the process of inserting the respective hook portions 22 into the hook holes 61.

If the sizes of the hook portion 22 and the hook hole 61 are not matched, the tip portion 22c of the hook portion 22 may be processed and made shorter or finer using a dental drill, etc., in the actual situation of treatment.

Thereafter, the abutment body 3 is capped onto the implant bodies 2. Specifically, the shaft portion insertion hole portions 31, provided in the abutment body 3, are fitted so as to cover the respective shaft portions 21 from the axial direction. In this state, the respective shaft portions 21 of the implant bodies 2 are housed tightly in the shaft portion insertion hole portions 31a of the abutment body 3.

Thereafter, the fixing member 4 is inserted continuously in a bolt-like manner in the hole portions 21a and the side hole surface portion 32 respectively provided in the implant bodies 2 and the abutment body 3. The implant bodies 2 and the abutment body 3 are thereby fixed.

If a gap forms between the implant body 2 and the abutment body 3 or between the hole portion 21a or the side surface hole portion 32 and the fixing member 4, the gap may be filled with dental cement, etc., and it is preferable for the implant bodies 2, the abutment body 3, and the fixing member 4 to be fixed integrally without any gaps.

Lastly, the artificial tooth 5 is capped onto the integrated body of the implant bodies 2 the abutment body 3, and the fixing member 4. In this process, the abutment body 3 may be processed in accordance with the artificial tooth 5 and arranged in shape so that the two fit together and further, the two may be fixed by adhesion using a dental adhesive or dental cement, etc.

With the artificial tooth implant device 1 according to the present invention, the implant bodies 2 can be mounted on the jawbone 6 by hooking the hook portions 22, provided on the implant bodies 2, in the hook holes 61 bored in the jawbone 6, and therefore a period for integration of the implant bodies 2 and the jawbone 6 is not required as in the conventional implant treatment and the treatment period and the number of times of treatment, can be reduced. If treatment is hurried, the procedures from the boring of the hook holes 61 in the jawbone 6 to the mounting of the implant bodies 2 and the abutment body 3 can be performed even on the same day as tooth extraction. If it is possible to prepare an artificial tooth 5 that fits the patient on the same day, the treatment can be completed on the same day as the tooth extraction. Even if the artificial tooth 5 is to be completed at a later date, the treatment can be completed in two times of treatment—that of tooth extraction to mounting of the implant, bodies 2, etc., and that of mounting of the artificial tooth 5.

Also, the hook portion of each implant body 2, with a diameter of no more than 3 mm, is an extra-fine member approximate to an injection needle and therefore enables treatment, from the boring of the hook holes 61 to the mounting of the implant bodies 2, to be performed from above the gum 7 and without cutting the gum 7 so that bleeding can be suppressed to the minimum and the physical and mental pain and burden inflicted on a patient can be minimized.

Further, the hook portion 22 is mounted shallowly and obliquely onto the jawbone 6 so that the minimum bone thickness or bone amount suffices at the mounting location, and especially in cases of the upper jaw, etc, treatment is made possible for patients who would have required an auxiliary operation with the conventional implant treatment and the number of times of treatment and treatment time can be reduced correspondingly,

INDUSTRIAL APPLICABILITY

By using the artificial tooth implant device 1 according to the present invention, the treatment period and the number of times of treatment can be reduced for many patients, regardless of the bone amount, etc., of the jawbone 8, and the impacts to the entire oral cavity, including the jawbone 6 and the gum 7, can be minimized so that use can be made in dental implant treatments that can lighten the mental and physical burden of a patient.

DESCRIPTION OF THE SYMBOLS

1: Artificial tooth implant device
2: Implant body
21: Shaft portion
21a: Hole portion
22: Hook portion
22a: Upper portion
22b: Lower portion
22c: Tip portion
22d: Step portion
23: Divided cylindrical shaft portion
23a: Hole portion
24: Joined cylindrical shaft portion
25: Male thread
3: Abutment body
31: Shaft insertion hole portion
32: Side surface hole portion
33: Side surface groove portion
34: Latching hole portion
35: Female thread portion
4: Fixing member 5: Artificial tooth
6: Jawbone
61: Hook hole
62: Hook hole step portion
7: Gum
S: Gap
T: Natural tooth

What is claimed is:

1. An implant for an artificial tooth, comprising:
first and second implant bodies forming a pair, each of said implant bodies including a shaft portion, a hook portion extending from the respective shaft portion, and a tip portion, each said hook portion being configured to be hooked in a hole in a jawbone of a patient, being bent with respect to the respective shaft portion and having a dogleg shape, each said dogleg shape having an upper portion and a lower portion with upper and lower longitudinal axes extending along respective centers thereof, respectively, at respective acute angles relative to one another and to the respective shaft portion, said upper and said lower portions extending end to end along said longitudinal axes thereof, each said tip portion being on a respective end of the respective hook portion remote from said shaft portion thereof and facing and extending inwardly toward each other; and
a fixing part connecting said first and said second implant bodies and being attached securely to only a single artificial tooth.

2. The implant according to claim 1 wherein
each of the upper and the lower portions comprises an elongated member.

3. The implant according to claim 1 wherein
a step portion is provided between each said hook portion and the respective tip portion, each said tip portion having a smaller transverse diameter than an adjacent portion of the respective hook portion.

4. The implant according to claim 1 wherein
said fixing part comprises first and second hole portions receiving said shaft portions of said first and said second implant bodies, respectively; and
a fixing member extends through aligned holes in said fixing part and in said shaft portions fixing said fixing part and said implant bodies to each other.

5. The implant according to claim 4 wherein
said fixing member and said aligned holes in said fixing part and said shaft portions extend perpendicularly to longitudinal axes of said shaft portions.

6. The implant according to claim 4 wherein
said fixing part comprises an abutment body; and
said aligned holes in said fixing part are in side surfaces of said abutment body.

7. The implant according to claim 1 wherein
third and fourth implant bodies each comprise a shaft portion, a hook portion extending from the respective shaft portion and a tip portion, each said hook portion of said third and said fourth implant bodies being configured to be hooked in a respective hole in the jawbone of the patient, being bent with respect to the respective shaft portion and having the dogleg shape, said tip portions of said third and said fourth implant bodies being on ends of the respective hook portion remote from the respective shaft portions and facing and extending toward each other; and
said shaft portions of said third and said fourth implant bodies being connected to said fixing part.

8. The implant according to claim 7 wherein
each of said upper and said lower portions comprises an elongated member.

9. The implant according to claim 7 wherein
a step portion is provided between each said hook portion and the respective tip portion, each said tip portion having a smaller transverse diameter than an adjacent portion of the respective hook portion.

10. The implant according to claim 7 wherein
said fixing part comprises first, second, third and fourth hole portions receiving said shaft portions of said first, said second, said third and said fourth implant bodies, respectively; and
first and second fixing members extend through first and second sets of aligned holes in said fixing part and in said shaft portions of said first and said second implant bodies and said third and said fourth implant bodies, respectively, fixing said fixing part and said implant bodies to each other.

11. The implant according to claim 10 wherein
said fixing member and said aligned holes in said fixing part and said shaft portions extend perpendicularly to longitudinal axes of said shaft portions.

12. The implant according to claim 1 wherein
each said shaft portion has a half thread on an outer surface thereof; and
said fixing part has a female thread on an inner surface thereof threadedly engaged with each said half thread.

13. The implant according to claim 1 wherein
said upper and said lower portions are each cylindrical.

14. The implant according to claim 1 wherein
said upper portion is conically tapered in a direction toward said tip portion.

15. The implant according to claim 1 wherein
each of said hook portions consists of said upper portion and said lower portion.

* * * * *